United States Patent
Misske et al.

(10) Patent No.: US 11,254,648 B2
(45) Date of Patent: Feb. 22, 2022

(54) PROCESS FOR PRODUCING GLYCEROL CARBONATE METHACRYLATE

(71) Applicant: BASF SE, Ludwigshafen am Rhein (DE)

(72) Inventors: Andrea Misske, Ludwigshafen am Rhein (DE); Christoph Fleckenstein, Ludwigshafen am Rhein (DE); Matthias Klueglein, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 66 days.

(21) Appl. No.: 16/771,885

(22) PCT Filed: Dec. 7, 2018

(86) PCT No.: PCT/EP2018/084013
§ 371 (c)(1),
(2) Date: Jun. 11, 2020

(87) PCT Pub. No.: WO2019/115399
PCT Pub. Date: Jun. 20, 2019

(65) Prior Publication Data
US 2021/0070729 A1 Mar. 11, 2021

(30) Foreign Application Priority Data

Dec. 15, 2017 (EP) .................................... 17207791

(51) Int. Cl.
*C07D 317/38* (2006.01)
(52) U.S. Cl.
CPC .................. *C07D 317/38* (2013.01)
(58) Field of Classification Search
CPC .................................................. C07D 317/38
See application file for complete search history.

(56) References Cited

U.S. PATENT DOCUMENTS

| 4,892,954 A | 1/1990 | Brindöpke et al. |
| 2019/0169346 A1 | 6/2019 | Misske et al. |
| 2019/0375954 A1 | 12/2019 | Fleckenstein et al. |
| 2020/0231528 A1 | 7/2020 | Blanchot et al. |

FOREIGN PATENT DOCUMENTS

| EP | 0212409 A2 | 3/1987 |

OTHER PUBLICATIONS

Amaral et al. (Synthesis of bifunctional cyclic carbonates from CO2 catalysed by choline-based systems. Tetrahedron Lett. 54 (2013) 5518-5522).*
International Search Report for PCT/EP2018/084013 dated Feb. 14, 2019.
Written Opinion of the International Searching Authority for PCT/EP2018/084013 dated Feb. 14, 2019.
Axelsson, et al., "Centrifuges, Sedimenting", Ullmann's Encyclopedia of Industrial Chemistry, vol. 7, Jul. 15, 2006, pp. 493-520.
European Search Report for EP Patent Application No. 17207791.9, dated Mar. 20, 2018, 4 pages.
International Preliminary Report on Patentability received for PCT Patent Application No. PCT/EP2018/084013, dated Jun. 25, 2020, 12 pages. (6 pages of English Translation and 6 pages of Original Document).
Muller, "Liquid-Liquid Extraction" Ullmann's Encyclopedia of Industrial Chemistry, vol. 21, Jan. 15, 2007, pp. 249-307.
Ripperger, et al., "Filtration, 1 Fundamentals", Ullmann's Encyclopedia of Industrial Chemistry, Sep. 16, 2013, pp. 1-38.
Ripperger, et al., "Filtration, 2 Equipment", Ullmann's Encyclopedia of Industrial Chemistry, Oct. 9, 2013, pp. 1-40.
Song, et al., "Highly efficient synthesis of cyclic carbonates from CO2 and epoxides catalyzed by KI/lecithin", Catalysis Today, vol. 183, Issue 1, Mar. 20, 2012, pp. 130-135.
Urs A. Peuker, "Cenliituges, Filtering" Ullmann's Encyclopedia of Industrial Chemistry, vol. 7, Jan. 15, 2007, pp. 471-492.
US application filed Aug. 9, 2019, U.S. Appl. No. 16/484,914.
U.S. application filed Dec. 13, 2019, U.S. Appl. No. 16/622,474.
U.S. application filed Jul. 27, 2019, U.S. Appl. No. 16/480,703.
U.S. Appl. No. 16/061,496.
U.S. Appl. No. 62/272,700.
Werner, et al., "Hydroxyl-Functionalized Imidazoles: Highly Active Additives for the Potassium Iodide-Catalyzed Synthesis of 1,3-Dioxolan-2-one Derivatives from Epoxides and Carbon Dioxide", ChemcatChem Catalysis, vol. 6, Issue 12, Oct. 10, 2014, pp. 3493-3500.
Werner, et al., "Synthesis of cyclic carbonates from epoxides and CO2 catalyzed by potassium iodide and amino alcohols", Journal of CO2 Utilization, vol. 7, Sep. 2014, pp. 39-45.

* cited by examiner

*Primary Examiner* — Valerie Rodriguez-Garcia
(74) *Attorney, Agent, or Firm* — Faegre Drinker Biddle & Reath LLP

(57) ABSTRACT

A process for preparing glycerol carbonate methacrylate, wherein glycidyl methacrylate is reacted with carbon dioxide in the presence of a catalyst and a solvent, wherein the catalyst is potassium iodide, the solvent is acetonitrile, one or more monoalcohols, or any desired mixture of acetonitrile and one or more monoalcohols, and the reaction of glycidyl methacrylate with carbon dioxide is carried out at a pressure from 0.5 to 5 bar.

16 Claims, No Drawings

PROCESS FOR PRODUCING GLYCEROL CARBONATE METHACRYLATE

CROSS-REFERENCE TO RELATED APPLICATIONS

This application is a national stage application (under 35 U.S.C. § 371) of PCT/EP2018/084013, filed Dec. 7, 2018, which claims benefit of European Application No. 17207791.9, filed Dec. 15, 2017, both of which are incorporated herein by reference in their entirety.

The present invention relates to a process for preparing glycerol carbonate methacrylate (GCMA). In the process according to the invention, glycidyl methacrylate (GMA) is reacted with carbon dioxide in the presence of potassium iodide as catalyst.

Glycerol carbonate methacrylate is used, for example, in the production of copolymers. In addition to glycerol carbonate methacrylate, these copolymers preferably also comprise acrylates, methacrylates, and/or vinyl monomers in copolymerized form.

The reactivity of the carbonate group of the copolymerized glycerol carbonate methacrylate makes it possible to modify copolymers comprising glycerol carbonate methacrylate and thus to alter their properties in a targeted manner.

Thus, copolymers that comprise glycerol carbonate methacrylate as a comonomer in copolymerized form are used, for example, as crosslinkers. The carbonate group of copolymerized glycerol carbonate methacrylate allows, for example, crosslinking reactions with polymers bearing free amino groups, hydrazide groups, hydrazone groups, carboxylic acid groups, anhydride groups, and/or hydroxyl groups.

Prior art processes for preparing glycerol carbonate methacrylate through the reaction of glycidyl methacrylate with carbon dioxide in the presence of a catalyst are known to those skilled in the art. The catalysts used are mostly iodides and/or amine compounds. Depending on the catalysts used, the reaction may be carried out at atmospheric pressure or elevated pressure.

The object was to provide an improved process for preparing glycerol carbonate methacrylate. The improved process should make it possible to prepare glycerol carbonate methacrylate with high selectivity at low pressures using an easily accessible catalyst such as potassium iodide. More rapid conversion of the GMA used into GCMA should also be possible. Low pressures in this context are pressures of 0.5 to 5, preferably 0.8 to 1.5, and more preferably 0.8 to 1.2 bar. High selectivity is selectivity above 95%, preferably above 97%, most preferably above 97.5%.

The object is achieved by a process for preparing glycerol carbonate methacrylate, wherein glycidyl methacrylate is reacted with carbon dioxide in the presence of a catalyst and a solvent, wherein the catalyst is potassium iodide, the solvent is acetonitrile, one or more monoalcohols, or any desired mixture of acetonitrile and one or more monoalcohols, and the reaction of glycidyl methacrylate with carbon dioxide is carried out at a pressure from 0.5 to 5 bar.

Definitions

The abbreviation GMA stands for glycidyl methacrylate (2,3-epoxypropyl methacrylate).

The abbreviation GCMA stands for glycerol carbonate methacrylate (2-oxo-1,3-dioxolan-4-yl)methyl methacrylate.

The selectivity is calculated from the following formula:

$$\text{Selectivity}(\%) = \frac{GCMA\ (\text{area}\%) \times 100}{GCMA\ (\text{area}\%) + \sum \text{By-products}\ (\text{area}\%)}$$

The process according to the invention is used to prepare GCMA through the reaction of GMA with carbon dioxide in the presence of potassium iodide as catalyst and a solvent. Carbon dioxide is preferably supplied to a reaction mixture comprising the catalyst, the solvent, GMA that has not yet reacted, and optionally any GCMA already formed.

The process according to the invention may be carried out as a continuous or batchwise operation, with a batchwise operation being preferred. If carried out as a batchwise process, it is advantageous when the reactor is initially charged with GMA, the catalyst, and the solvent. Carbon dioxide is then supplied to the initially charged reaction mixture.

Suitable reactors for the process according to the invention may be any reactor type known to those skilled in the art for continuous or batchwise processes. If the process according to the invention is carried out as a batchwise operation, stirred-tank reactors are particularly suitable. It is possible to connect more than one reactor in series and/or in parallel, preferably stirred-tank reactors if being operated in a batchwise process.

The reaction of GMA with carbon dioxide is carried out at a pressure from 0.5 to 5 bar. The reaction is preferably carried out at a pressure from 0.8 to 1.5 bar. The reaction is more preferably carried out at a pressure from 0.8 to 1.2 bar.

The reaction of GMA with carbon dioxide is carried out preferably at a temperature from 50 to 100° C. and more preferably at a temperature from 75 to 100° C.

It is accordingly preferable that the reaction of GMA with carbon dioxide is carried out at a pressure from 0.8 to 1.5 bar and a temperature from 50 to 100° C. and in particular at a pressure from 0.8 to 1.5 bar and a temperature from 75 to 100° C.

The process according to the invention preferably uses the purest possible glycidyl methacrylate. The purest possible GMA has a purity of 95 to 100 percent by weight. It is further preferable that the GMA used in the process according to the invention has a purity from 97 to 100 percent by weight and particularly preferably a purity from 99 to 100 percent by weight Percentages by weight are based on the total amount of GMA used.

The GMA used in the process according to the invention may already comprise one or more polymerization stabilizers. If the GMA used already comprises one or more polymerization stabilizers, these are present in effective concentrations. For example, the GMA used may contain 20 to 1000 ppm, preferably 50 to 300 ppm, and more preferably 80 to 120 ppm, of polymerization stabilizers. Values in ppm are based on the total amount by weight of polymerization stabilizer present in the GMA used.

Suitable polymerization stabilizers are known to those skilled in the art or may be established by them based on their specialist knowledge. Examples of suitable polymerization stabilizers are copper (meth)acrylates, copper dithiocarbamates, phenothiazines, phenolic compounds, N-oxyls, phenylenediamines, nitroso compounds, ureas or thioureas. These polymerization stabilizers may be used individually or in the form of any desired mixture. Preferred stabilizers are phenothiazines, phenolic compounds, N-oxyls or any desired mixtures thereof.

Examples of phenothiazines are phenothiazine, bis(α-methylbenzyl)phenothiazine, 3,7-dioctylphenothiazine, bis(α-dimethylbenzyl)phenothiazine or any desired mixture thereof.

Examples of phenolic compounds are hydroquinone, hydroquinone monomethyl ether, such as para-methoxyphenol (MEHQ), pyrogallol, catechol, resorcinol, phenol, cresol, 2,4-dimethyl-6-tert-butylphenol, 2,6-di-tert-butyl-para-cresol or any desired mixture thereof. Preferred phenolic compounds are para-methoxyphenol (MEHQ), 2,4-dimethyl-6-tert-butylphenol, 2,6-di-tert-butyl-para-cresol or any desired mixture thereof.

Examples of N-oxyls include di-tert-butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidinoxyl, 4-hydroxy-2,2,6,6-tetramethylpiperidinoxyl, 4,4',4"-tris-1-(2,2,6,6-tetramethylpiperidinoxyl)phosphites or any desired mixture thereof.

In the process according to the invention, potassium iodide is used as catalyst. It is preferable that the molar ratio between the total amount of catalyst used and the total amount of GMA used is 0.005:1 to 0.5:1. It is further preferable that the molar ratio is 0.01:1 to 0.3:1.

The solvent is acetonitrile, one or more monoalcohols or any desired mixture of acetonitrile and one or more monoalcohols.

It is preferable that the total amount of solvent used is 0.1 to 50 percent by weight based on the total amount of GMA used. It is further preferable that the total amount of solvent used is 0.5 to 40 percent by weight based on the total amount of GMA used.

A monoalcohol is a monohydric alkyl alcohol. The monoalcohol is preferably ethanol, n-propanol, isopropanol, n-butanol, sec-butanol, isobutanol or tert-butanol. The monoalcohol is particularly preferably tert-butanol.

It is particularly preferable that acetonitrile is used as solvent in an amount of 0.5 to 40 percent by weight based on the total amount of GMA used. In particular, it is preferable that acetonitrile is used as solvent in an amount of 2 to 40 percent by weight based on the total amount of GMA used.

Carbon dioxide is supplied to the process according to the invention continuously or intermittently. It is preferable that carbon dioxide is supplied to the process according to the invention continuously. Continuous supply of carbon dioxide is particularly preferable when the process according to the invention is carried out as a batchwise operation.

The molar ratio between the total amount of carbon dioxide used and the total amount of GMA used is preferably 1:1 to 100:1. It is further preferable that the molar ratio is 1:1 to 10:1.

The carbon dioxide supply rate may vary over a wide range. It is generally advantageous to adjust the carbon dioxide supply rate such that the proportion of carbon dioxide in the gas stream discharged from the reaction is as low as possible. The carbon dioxide supply rate may vary over the course of the reaction.

The carbon dioxide supply rate is preferably 1 to 100 $L(CO_2)/(kg(GMA_{total\ amount\ used})h)$, more preferably 10 to 60 $L(CO_2)/(kg(GMA_{total\ amount\ used})h)$, particularly preferably 10 to 30 $L(CO_2)/(kg(GMA_{total\ amount\ used})h)$.

Carbon dioxide is preferably supplied to the process according to the invention in the form of a carbon dioxide-containing gas. The carbon dioxide-containing gas is fed into the reaction mixture comprising the catalyst, the solvent, GMA that has not yet reacted, and optionally any GCMA already formed, and/or into the gas space above the reaction mixture. It is preferable that the carbon dioxide-containing gas is fed in continuously.

The supply rate of the carbon dioxide-containing gas may vary over a wide range. It is generally advantageous to adjust the supply rate of the carbon dioxide-containing gas such that the proportion of carbon dioxide in the gas stream discharged from the reaction is as low as possible. The supply rate of the carbon dioxide-containing gas may vary over the course of the reaction.

The supply rate of the carbon dioxide-containing gas is preferably 1 to 100 $L(CO_2)/(kg(GMA_{total\ amount\ used})h)$, more preferably 10 to 60 $L(CO_2)/(kg(GMA_{total\ amount\ used})h)$, particularly preferably 10 to 30 $L(CO_2)/(kg(GMA_{total\ amount\ used})h)$.

The carbon dioxide-containing gas may be fed into the reaction mixture via, for example, one or more dip tubes or one or more nozzles. The openings of the dip tubes or nozzles are in this case below the surface of the reaction mixture. If the carbon dioxide-containing gas is fed into the gas space above the reaction mixture, this is done via, for example, one or more feed tubes or one or more nozzles. The openings of the feed tubes or nozzles are in this case situated above the surface of the reaction mixture.

If the process is carried out as a batchwise operation, the carbon dioxide-containing gas may be fed in before heating the initially charged reaction mixture to a temperature from 50 to 100° C., during heating, and/or after reaching the target temperature. The carbon dioxide-containing gas is preferably fed in for the entire duration of the process. This means that the carbon dioxide-containing gas is already being fed in before or during the heating of the reaction mixture and the feeding of the carbon dioxide-containing gas is not ended until the GMA used has been mostly converted into GCMA. "Mostly" in this context means that 90 to 100 percent by weight, preferably 95 to 100 percent by weight, more preferably 98 to 100 percent by weight, of the GMA used has been converted into GCMA.

In addition to carbon dioxide, the carbon dioxide-containing gas may also comprise one or more gases other than carbon dioxide. Examples of gases other than carbon dioxide are inert gases, such as nitrogen, argon or helium; or oxygen.

The proportion of carbon dioxide in the carbon dioxide-containing gas is preferably 1 to 100 percent by volume based on the total amount of the carbon dioxide-containing gas used. It is further preferable that the carbon dioxide content in the carbon dioxide-containing gas is 50 to 100, and particularly preferably 90 to 100, percent by volume.

The total proportion of one or more gases present in the carbon dioxide-containing gas other than carbon dioxide is preferably 0 to 99 percent by volume based on the total amount of the carbon dioxide-containing gas used. It is further preferable that the total proportion of one or more gases is 0 to 50, and particularly preferably 0 to 10, percent by volume.

It is generally possible, although not preferable, that the carbon dioxide-containing gas also comprises, in addition to one or more inert gases and/or oxygen, traces of other gaseous substances such as hydrogen, water, methane and/or carbon monoxide. The sum of all gases present in the carbon dioxide-containing gas, including gaseous substances, adds up to 100 percent.

It is preferable that an oxygen-containing gas is fed into the process according to the invention. It is preferable that the oxygen-containing gas comprises, in addition to oxygen, one or more gases other than oxygen. Supplying an oxygen-containing gas serves to minimize undesired polymerization of the GMA used or of the GCMA produced.

The oxygen-containing gas may be fed into the process continuously or intermittently. It is preferable that the oxygen-containing gas is supplied to the process according to the invention continuously. Continuous supply of an oxygen-containing gas is particularly preferable when the process according to the invention is carried out as a batchwise operation.

The oxygen content in the oxygen-containing gas is preferably 1 to 25 percent by volume based on the total amount of the oxygen-containing gas used. It is further preferable that the oxygen content in the oxygen-containing gas is 5 to 25, and particularly preferably 10 to 22, percent by volume.

The total proportion of one or more gases present in the oxygen-containing gas other than oxygen is preferably 75 to 99 percent by volume based on the total amount of the oxygen-containing gas used. It is further preferable that the total proportion of one or more gases is 75 to 95, and particularly preferably 78 to 90, percent by volume. Examples of gases other than oxygen are nitrogen, argon, helium or carbon dioxide. The proportion of carbon dioxide in the oxygen-containing gas is less than 1 percent by volume.

Examples of preferred oxygen-containing gases are air, dried air or lean air.

The supply rate of the oxygen-containing gas may vary over a wide range. The feed rate is preferably 0.1 to 1, more preferably 0.3 to 0.8, and particularly preferably 0.2 to 0.4, $m^3/m^3_{(reaction\ mixture)}h)$.

When the oxygen-containing gas is fed into the process according to the invention, it is preferable that the oxygen-containing gas be fed into the reaction mixture and/or into the gas space above the reaction mixture. The oxygen-containing gas may be fed into the reaction mixture via, for example, one or more dip tubes or one or more nozzles. The openings of the dip tubes or nozzles are in this case below the surface of the reaction mixture. When the oxygen-containing gas is fed into the gas space above the reaction mixture, this is done via, for example, one or more feed tubes or one or more nozzles. The openings of the feed tubes or nozzles are in this case situated above the surface of the reaction mixture.

It is accordingly particularly preferable that the oxygen-containing gas is fed into the reaction mixture and/or into the gas space above the reaction mixture continuously.

The carbon dioxide-containing gas and the oxygen-containing gas may be introduced into the reaction mixture and/or into the gas space above the reaction mixture independently of one another.

If the process is carried out as a batchwise operation, the oxygen-containing gas may be fed in before heating the initially charged reaction mixture to a temperature from 50 to 100° C., during heating, and/or after reaching the target temperature. The oxygen-containing gas is preferably fed in for the entire duration of the process. This means that the oxygen-containing gas is already being fed in before or during the heating of the reaction mixture and the feeding of the oxygen-containing gas is not ended until the GMA used has been mostly converted into GCMA. "Mostly" in this context means that 90 to 100 percent by weight, preferably 95 to 100 percent by weight, more preferably 98 to 100 percent by weight, of the GMA used has been converted into GCMA.

In order to avoid undesired polymerization of the GMA used and/or of the GCMA produced during the process according to the invention, it is preferable, irrespective of whether the GMA used comprises one or more polymerization stabilizers, that the reaction of GMA with carbon dioxide to GCMA is carried out in the presence of one or more (additional) polymerization stabilizers.

Suitable polymerization stabilizers are the abovementioned polymerization stabilizers, with preference given to MeHQ and/or phenothiazine.

The total amount of polymerization stabilizer used in the process according to the invention is preferably 0.005 to 0.15 and more preferably 0.05 to 0.15 percent by weight based on the total amount of GMA used, with the amount of stabilizer present in the GMA being disregarded.

If the GMA used has been mostly converted to GCMA, the resulting reaction mixture is worked up in order to isolate GCMA from the reaction mixture. "Mostly" in this context means that 90 to 100 percent by weight, preferably 95 to 100 percent by weight, more preferably 98 to 100 percent by weight, of the GMA used has been converted into GCMA.

The workup of the reaction mixture comprises one or more extraction steps and/or one or more distillation steps. In order to at least mostly remove the catalyst from the reaction mixture, it may be advantageous for the workup to additionally comprise one or more filtration, centrifugation, absorption, and/or sedimentation steps. In order to at least partially destroy any GMA still present in the reaction mixture, it may be advantageous for the workup to additionally include the addition of one or more acids, for example formic acid, acetic acid, phosphoric acid, and/or phosphinic acid, with preference given to phosphoric acid and/or phosphinic acid. The addition of one or more acids has the advantage that GCMA present in the reaction mixture is not destroyed or is destroyed only to a small extent. One or more distillation steps may be employed to remove compounds more volatile than GCMA.

For the sequence of the abovementioned process steps for workup of the reaction mixture, those skilled in the art may be guided by practical considerations.

For example, the reaction mixture may be filtered, one or more acids added to the filtrate, the resulting mixture extracted in one or more steps, and the resulting organic phase distilled in one or more steps.

However, it is also possible for one or more acids to be added to the reaction mixture before the filtration or after the extraction. It is also possible to additionally add one or more acids to the GCMA present in the bottoms after the distillation. This can, for example, have a beneficial effect on the color of the GCMA present in the bottoms.

For workup of the reaction mixture, the acid used may be in concentrated form or in the form of an aqueous solution thereof. Formic acid, acetic acid, phosphoric acid or phosphinic acid used for workup of the reaction mixture may be in concentrated form or in the form of an aqueous solution thereof, for example a 1 to 99 percent aqueous solution. Percent values are based on the total weight of aqueous acid solution added. Preference is given to adding phosphoric acid and/or phosphinic acid to the reaction mixture in the form of aqueous solutions thereof.

The total amount of acid used in workup is guided by the amount of residual GMA still present in the reaction mixture. The amount of residual GMA still present in the reaction mixture may be detected and quantified by, for example, GC methods. For reliable quantitation of GMA traces <0.2%, HPLC and UPLC methods may also be used. It is preferable to calculate the total amount of acid(s) used such that they are added to the reaction mixture in a stoichiometric excess of 5 to 1000 percent based on the amount of residual GMA still present in the reaction mixture.

The addition of one or more acids to the reaction mixture is preferably carried out at a temperature from 10° C. to 100° C. More preferably, the addition of one or more acids to the reaction mixture is carried out at a temperature from 10° C. to 60° C. and particularly preferably at a temperature from 30° C. to 50° C.

It is particularly preferable to add phosphoric acid and/or phosphinic acid at a temperature from 10° C. to 100° C. and in particular at a temperature from 30° C. to 50° C.

In terms of process engineering, it is possible to use in the process of the invention any filtration methods and apparatuses known per se, for example those described in Ullmann's Encyclopedia of Industrial Chemistry, 7th ed., 2013 electronic release, chapter: Filtration, 1. Fundamentals and Filtration 2. Equipment. For example, these may be cartridge filters, filter presses, pressure-plate filters, bag filters or drum filters. Preference is given to using cartridge filters or pressure-plate filters. The filtration may be carried out with or without filtering aids. Suitable filtering aids are filtering aids based on kieselguhr, perlite, and cellulose.

In terms of process engineering, it is possible to use in the process of the invention any centrifugation methods and apparatuses and sedimentation methods and apparatuses known per se, for example those described in Ullmann's Encyclopedia of Industrial Chemistry, 7th ed., 2013 electronic release, chapter: Centrifuges, Filtering and Centrifuges, Sedimenting.

In an extraction step, the reaction mixture is mixed with water and the phases are then separated. The ratio of water to reaction mixture that is employed for the extraction may vary over a wide range. Advantageous ratios may be determined by those skilled in the art by means of a few routine tests or established by them based on their specialist knowledge or on the basis of practical considerations.

The water may additionally contain a dissolved salt. The additional salt may for example be sodium chloride, potassium chloride, ammonium chloride, ammonium sulfate, or any desired mixtures thereof. The salt is preferably sodium chloride. The amount of the salt corresponds to the customary amounts used for extractions. Advantageous amounts may be determined by those skilled in the art by means of a few routine tests or established by them based on their specialist knowledge or on the basis of practical considerations.

The water or aqueous solution of a salt is added at a temperature from 10 to 70° C., preferably at a temperature from 40 to 60° C.

An organic solvent that is sparingly soluble in water may additionally be added to the reaction mixture. This may be done, for example, to facilitate phase separation. An organic solvent that is sparingly soluble in water has a solubility in water of less than 10 g/l of water at 20° C., preferably less than 1 g/l of water at 20° C.

The ratio of reaction mixture to aqueous solution of a salt may vary over a wide range. Advantageous ratios may be determined by those skilled in the art by means of a few routine tests or established by them based on their specialist knowledge or on the basis of practical considerations.

In terms of process engineering, it is possible to use for an extraction in the process of the invention any extraction and washing methods and apparatuses known per se, for example those described in Ullmann's Encyclopedia of Industrial Chemistry, 6th ed., 1999 electronic release, chapter: Liquid-Liquid Extraction-Apparatus. For example, these may be single-stage or multistage, preferably single-stage, extractions and also extractions in cocurrent or countercurrent mode. Examples of vessels that are suitable for the extraction are stirred vessels, columns or mixer-settler apparatuses.

In a distillation step, the compounds that are more volatile than GCMA are at least mostly removed from the reaction mixture by distillation. GCMA is left behind as the bottoms fraction.

Suitable apparatuses for the removal by distillation of the more volatile compounds are in general all apparatuses for the separation by distillation of reaction mixtures comprising liquid components. Suitable apparatuses include distillation columns such as tray columns, which may be equipped with bubble-cap trays, sieve plates, sieve trays, ordered packings or random packings, or spinning-band column evaporators, such as thin-film evaporators, falling-film evaporators, forced-circulation evaporators, Sambay evaporators etc., and combinations thereof. One or more distillation steps may be connected in series. The distillation steps may take place in identical or different apparatuses.

When choosing suitable temperature and pressure ranges for the removal by distillation of lower-boiling compounds, those skilled in the art may be guided by the physical conditions of the separation task (for example vapor pressure curves) and also by their specialist knowledge and by practical considerations.

Advantageously, the GCMA produced by the process according to the invention does not itself need to undergo purification by distillation or rectification in order to isolate GCMA in high purity. This means that GCMA may be isolated using relatively simple apparatus. The thermal stress on the GCMA during isolation is also reduced, as a result of which the formation of by-products can be minimized. High purity in this context means that the proportion of by-products in the GCMA is 0 to 5 percent by weight, preferably 0 to 3 percent by weight, and more preferably 0 to 2 percent by weight, based on the total amount of GCMA isolated.

To further reduce the color value of the GCMA produced by the process according to the invention, it may be advantageous for the GCMA to be distilled or rectified. This may be done by isolating the GCMA from the reaction mixture directly, for example by distillation or rectification. If GCMA has been isolated by extraction and/or removal of lower-boiling compounds by distillation, the GCMA thus obtained may also undergo distillation or rectification. However, the process according to the invention generally affords GCMA having a sufficiently low color value, as a result of which distillation or rectification of the GCMA itself is not necessary.

The process according to the invention has the advantage that GCMA may be produced with high selectivity at low pressures and using an easily obtainable catalyst. The process according to the invention thus represents an economically attractive process for preparing GCMA.

A further advantage of the process according to the invention is, for example, that GCMA may be produced in high quality. High quality of the GCMA prepared by the process according to the invention is demonstrated, for example, by high purity and/or a low color value.

GCMA prepared by the process according to the invention is suitable, for example, for the production of copolymers. In addition to glycerol carbonate methacrylate, these copolymers preferably also comprise acrylates, methacrylates, and/or vinyl monomers in copolymerized form.

The reactivity of the carbonate group of the copolymerized GCMA makes it possible to modify copolymers containing GCMA and thus to alter their properties in a targeted manner.

Thus, copolymers that comprise GCMA as a comonomer in copolymerized form are used, for example, as cross-linkers. The carbonate group of copolymerized GCMA allows, for example, crosslinking reactions with polymers bearing free amino groups, hydrazide groups, hydrazone groups, carboxylic acid groups, anhydride groups, and/or hydroxyl groups.

EXPERIMENTAL SECTION

The purity was determined by gas chromatography. The solvent used for the samples was dichloromethane from Aldrich, purity 99.8%.

The instrument used was a gas chromatograph from Agilent (6890N) with FID detector and RTX5 Amine 15 m×0.25 mm×0.25 μm column from Restek.

The following temperature program was set: 60° C. start, then 15° C./min to 300° C., 10 min at 300° C., total run time 26 min. Percent values for the purity and composition of the reaction solutions were determined in area percent by gas chromatography and were not quantified further. They are reported hereinbelow in area %.

Percent conversion values were calculated using the following formula:

$$\text{Conversion (\%)} = \frac{GCMA\ (\text{area\%}) \times 100}{GCMA\ (\text{area\%}) + GMA\ (\text{area\%})}$$

The GMA content in the ppm range was quantified by UPLC using an external standard. Values in ppm refer to mg/kg. The solvent used for the samples was acetonitrile/water in a volume ratio of 1:1. The instrument used was a UPLC from Waters with UV detector and Acquity UPLC BEH C18 1.7 μm 2.1×150 mm column from Waters. The eluents used were acetonitrile and water, with gradient elution (0.5 ml/min). Total run time 14 min, equilibration time 4 min, column temperature 45° C., and initial pressure approx. 11 000 psi.

The selectivity was determined using the following formula:

$$\text{Selectivity (\%)} = \frac{GCMA\ (\text{area\%}) \times 100}{GCMA\ (\text{area\%}) + \sum \text{By-products (area\%)}}$$

The Hazen color value and iodine color value were measured using a colorimeter for determination of color values from Hach Lange (Lico 620) and calculated for default illuminant C and 2° default observer in accordance with DIN 5033.

Reactants used:

| | Source | Purity | Stabilization |
|---|---|---|---|
| GMA | Novasol S.A. | >98 | 100 ± 20 ppm MeHQ |
| Carbon dioxide | Praxair | 99.9% | |
| Potassium iodide | Honeywell Sigma-Aldrich | >99.5% (analytical grade) | |
| Acetonitrile | Honeywell | >99.5% (GC) | |
| Phosphoric acid | Sigma-Aldrich | 85% in $H_2O$ | |
| Phosphinic acid | Sigma-Aldrich | 50% in $H_2O$ | |

INVENTIVE EXAMPLES

Example 1

A round-bottomed flask equipped with jacketed coil condenser, magnetic stirrer, thermometer, $CO_2$ inlet and with pressure equalization is charged with 7 mg of PTZ and 4.15 g of acetonitrile. To this is added 41.5 g of GMA and 4.75 g of KI. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 80.25%. The mixture comprises (excluding the solvent acetonitrile and disregarding components that do not pass through the GC) 79.38 area % of GCMA and 19.53 area % of GMA. The sum of the by-products is 1.09 area %. The selectivity is 98.6%. The reaction solution is colorless.

Example 2

A round-bottomed flask equipped with jacketed coil condenser, magnetic stirrer, thermometer, $CO_2$ inlet and with pressure equalization is charged with 7 mg of PTZ and 0.42 g of n-butanol. To this is added 41.5 g of GMA and 4.75 g of KI. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 82.7%. The mixture comprises (disregarding components that do not pass through the GC) 81.63 area % of GCMA and 17.04 area % of GMA. The sum of the by-products is 0.9 area %. The amount of n-butanol is 0.43 area %. The selectivity is 98.9%. The reaction solution is colorless.

Example 3

A round-bottomed flask equipped with jacketed coil condenser, magnetic stirrer, thermometer, $CO_2$ inlet and with pressure equalization is charged with 7 mg of PTZ and 2.08 g of sec-butanol. To this is added 41.5 g of GMA and 4.75 g of KI. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 84.3%. The mixture comprises (disregarding components that do not pass through the GC) 80.59 area % of GCMA and 15.04 area % of GMA. The sum of the by-products is 1.72 area %. The amount of sec-butanol is 2.65 area %. The selectivity is 97.9%. The reaction solution is colorless.

Example 4

A round-bottomed flask equipped with jacketed coil condenser, magnetic stirrer, thermometer, $CO_2$ inlet, and with pressure equalization is charged with 7 mg of PTZ and 2.08 g of acetonitrile. To this is added 41.5 g of GMA and 4.75 g of Kl. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 80.9%. The mixture comprises (excluding the solvent acetonitrile and disregarding components that do not pass through the GC) 80.03 area % of GCMA and 18.85 area % of GMA. The sum of the by-products is 1.12 area %. The selectivity is 98.6%. The reaction solution is colorless.

Example 5

A round-bottomed flask equipped with jacketed coil condenser, magnetic stirrer, thermometer, $CO_2$ inlet, and with pressure equalization is charged with 7 mg of PTZ and 2.08 g of isopropanol. To this is added 41.5 g of GMA and 2.37 g of Kl. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 8 h, the conversion of GMA into GCMA is 98.1%. The mixture comprises (excluding the solvent isopropanol and disregarding components that do not pass through the GC) 96.68 area % of GCMA and 1.91 area % of GMA. The sum of the by-products is 1.41 area %. The selectivity is 98.1%. The reaction solution is slightly yellowish.

Example 6

A round-bottomed flask equipped with jacketed coil condenser, magnetic stirrer, thermometer, $CO_2$ inlet, and with pressure equalization is charged with 7 mg of PTZ and 2.08 g of acetonitrile. To this is added 41.5 g of GMA and 4.75 g of finely ground Kl. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 80.3%. The mixture comprises (excluding the solvent acetonitrile and disregarding components that do not pass through the GC) 79.5 area % of GCMA and 19.56 area % of GMA. The sum of the by-products is 0.94 area %. The selectivity is 98.8%. The reaction solution is colorless.

Example 7

A round-bottomed flask equipped with jacketed coil condenser, magnetic stirrer, thermometer, $CO_2$ inlet, and with pressure equalization is charged with 7 mg of PTZ and 0.42 g of n-butanol. To this is added 41.5 g of GMA and 4.75 g of Kl. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 81.5%. The mixture comprises (disregarding components that do not pass through the GC) 80.45 area % of GCMA and 18.24 area % of GMA. The sum of the by-products is 0.99 area %. The amount of n-butanol is 0.32 area %. The selectivity is 98.8%. The reaction solution is colorless.

Example 8

A round-bottomed flask equipped with jacketed coil condenser, stirrer, thermometer, $CO_2$ inlet, and with pressure equalization is charged with 540 mg of MeHQ, 11 mg of PTZ, 72.9 g of Kl, and 238 g of acetonitrile. To this is added 425 g of GMA. $CO_2$ (approx. 5 L/h) and 1 L/h of air are fed into the reaction mixture. The reaction mixture is heated to an internal temperature from 80 to 85° C. Samples are collected at regular intervals and analyzed by gas chromatography. After 27 h, the conversion of GMA into GCMA is 99.4%. The reaction solution still contains 0.56 area % of GMA. After cooling, the reaction mixture is concentrated under reduced pressure and twice extracted with 50 ml of water, with phase separation. The organic phase is dried over sodium sulfate, filtered, and the filtrate is concentrated again under reduced pressure. 530 g (98.2% yield) of a light-colored liquid is obtained in a purity of 97.2 area %. The residual GMA content is 1.6 area %. The selectivity is 98.8%. The Hazen color value is 88.

Example 9

A round-bottomed flask equipped with jacketed coil condenser, stirrer, thermometer, $CO_2$ inlet, and with pressure equalization is charged with 1.14 g of MeHQ, 23 mg of PTZ, 103 g of Kl, and 504 g of acetonitrile. To this is added 900 g of GMA. $CO_2$ (approx. 30 L/h) and 1 L/h of air are fed into the reaction mixture. The reaction mixture is heated to an internal temperature from 80 to 85° C. Samples are collected at regular intervals and analyzed by gas chromatography. After 7 h, the feed rate is reduced to approx. 10 L/h. After 15 h, the conversion of GMA into GCMA is 99.11%. The reaction solution still contains 0.64 area % of GMA.

Example 10

2 g of a reaction mixture prepared in analogous manner to example 9 that has a conversion of GMA into GCMA of 99.41% and still contains 0.42 area % of GMA (0.5 area % without integration of the solvent acetonitrile) is mixed with 0.2 g of phosphinic acid (50% by weight) and the mixture is stirred at room temperature for 1.5 h. A sample is collected and analyzed by gas chromatography. There is still 0.07 area % of GMA remaining (without integration of the solvent).

Example 11

2 g of a reaction mixture prepared in analogous manner to example 9 that has a conversion of GMA into GCMA of 99.41% and still contains 0.42 area % of GMA (0.5 area % without integration of the solvent acetonitrile) is mixed with 0.2 g of phosphoric acid (85% by weight) and the mixture is stirred at room temperature for 1.5 h. There is still 0.11 area % of GMA remaining (without integration of the solvent).

Example 12

2 g of a reaction mixture prepared in analogous manner to example 9 that has a conversion of GMA into GCMA of 99.41% and still contains 0.42 area % of GMA (0.5 area % without integration of the solvent acetonitrile) is mixed with 0.2 g of acetic acid (99%) and the mixture is stirred at room temperature for 1.5 h. There is still 0.2 area % of GMA remaining (without integration of the solvent and of the acetic acid).

Example 13

2 g of a reaction mixture prepared in analogous manner to example 9 that has a conversion of GMA into GCMA of 99.41% and still contains 0.42 area % of GMA (0.5 area % without integration of the solvent acetonitrile) is mixed with 0.2 g of formic acid (98%) and the mixture is stirred at room temperature for 1.5 h. There is still 0.14 area % of GMA remaining (without integration of the solvent and the formic acid).

Example 14

A reaction mixture analogous to example 9 is cooled and then mixed with 12 g of phosphinic acid (50% by weight), stirred for 30 min, and filtered. The solution is concentrated under reduced pressure and twice extracted with 150 ml of water, with phase separation. It is then neutralized with aqueous $Na_2CO_3$ solution. After phase separation, the organic phase is concentrated again under reduced pressure. 1153 g of a light-colored liquid is obtained in a purity of 98.3 area %. The residual GMA content is <20 ppm (UPLC) The Hazen color value is 100.

Example 15

A heatable jacketed reactor equipped with jacketed coil condenser, disk stirrer, thermometer, $CO_2$ inlet, and with pressure equalization is charged with 2.8 g of MeHQ, 56 mg of PTZ, 252 g of Kl, and 1233 g of acetonitrile. To this is added 2200 g of GMA. $CO_2$ (approx. 40 L/h) and 1 L/h of air are fed into the reaction mixture. The reaction mixture is heated to an internal temperature from 85 to 90° C. Samples are collected at regular intervals and analyzed by gas chromatography. After 13 h, the conversion of GMA into GCMA is 99.46%. The reaction solution still contains 0.36 area % of GMA. Acetonitrile is distilled off under reduced pressure and the mixture is then cooled to 50° C. 500 ml of water is added and the mixture is extracted. The aqueous phase is removed. The reaction mixture is mixed with 36 g of phosphinic acid (50% by weight) and extracted twice with 500 ml of water at room temperature. The organic phase is neutralized with aqueous $Na_2CO_3$ solution and the aqueous phase is separated and concentrated under reduced pressure. 2798 g of a light-colored liquid is obtained in a purity of 98.7 area %. The residual GMA content is <20 ppm (UPLC) The Hazen color value is 32.

Example 16

A heatable jacketed reactor equipped with jacketed coil condenser, disk stirrer, thermometer, $CO_2$ inlet, and with pressure equalization is charged with 3.05 g of MeHQ, 348 mg of PTZ, 275 g of Kl, and 24 g of tert-butanol. To this is added 2400 g of GMA. $CO_2$ (approx. 35 L/h) and 1 L/h of air are fed into the reaction mixture. The reaction mixture is heated to an internal temperature from 90 to 95° C. Samples are collected at regular intervals and analyzed by gas chromatography. After 13 h, the conversion of GMA into GCMA is 99.65%. 871 g of $CO_2$ was used. The reaction solution still contains 0.34 area % of GMA. After cooling to 40° C., 500 ml of water is added and the mixture is extracted. The aqueous phase is removed. The reaction mixture is mixed with 31 g of phosphinic acid (50% by weight) and extracted two more times with 500 ml of water. The organic phase is neutralized with aqueous $Na_2CO_3$ solution and the aqueous phase is separated and concentrated under reduced pressure. A further 15 g of phosphinic acid (50% by weight) is added. 3059 g of a light-colored liquid is obtained in a purity of 98 area %. The residual GMA content is <20 ppm (UPLC) The Hazen color value is 34.

Example 17

A heatable jacketed reactor equipped with jacketed coil condenser, disk stirrer, thermometer, $CO_2$ inlet, and with pressure equalization is charged with 4.3 g of MeHQ, 86 mg of PTZ, 387 g of Kl, and 169 g of acetonitrile. To this is added 3386 g of GMA. $CO_2$ (approx. 40 L/h) and 1 L/h of air are fed into the reaction mixture. The reaction mixture is heated to an internal temperature from 90 to 95° C. Samples are collected at regular intervals and analyzed by gas chromatography. After 16 h, the conversion of GMA into GCMA is 99.44%. The reaction solution still contains 0.53 area % of GMA. After cooling to 60° C., 500 ml of water is added and the mixture is extracted. The aqueous phase is removed. The reaction mixture is mixed with 31 g of phosphinic acid (50% by weight) and extracted two more times with 500 ml of water at 40 to 50° C. The organic phase is neutralized with aqueous $Na_2CO_3$ solution and the aqueous phase is separated and concentrated under reduced pressure. 4299 g of a light-colored liquid is obtained in a purity of 98.3 area %. The residual GMA content is <20 ppm (UPLC) The Hazen color value is 193.

Example 18

A heatable jacketed reactor equipped with jacketed coil condenser, disk stirrer, thermometer, $CO_2$ inlet, and with pressure equalization is charged with 2.92 g of MeHQ, 58 mg of PTZ, 263 g of Kl, and 115 g of acetonitrile. To this is added 2300 g of GMA. $CO_2$ (approx. 50 to 70 L/h) is fed into the reaction mixture. The reaction mixture is heated to an internal temperature from 95 to 98° C. Samples are collected at regular intervals and analyzed by gas chromatography. After 7 h, the conversion of GMA into GCMA is 99.04%. 815 g of $CO_2$ was used. The reaction mixture is cooled and then mixed with 31 g of phosphinic acid (50% by weight), stirred for 30 min, and filtered. The solution is twice extracted with 500 ml of water at 40° C., with phase separation. The mixture is then neutralized with aqueous $Na_2CO_3$ solution and extracted again with 500 ml of water. After phase separation, 9 g of phosphinic acid (50% by weight) is added. After 20 min, the mixture is neutralized again with aqueous $Na_2CO_3$ solution, the phases are separated, and the organic phase is concentrated under reduced pressure. 2864 g of a light-colored liquid is obtained, which is filtered again. The purity is 98.5 area %. The residual GMA content is <20 ppm (UPLC) The Hazen color value is 20.

COMPARATIVE EXAMPLES

Example C1

A round-bottomed flask equipped with jacketed coil condenser, magnetic stirrer, thermometer, $CO_2$ inlet, and with pressure equalization is charged with 7 mg of PTZ. To this is added 41.5 g of GMA and 4.75 g of Kl. $CO_2$ (approx. 2 L/h) and 0.5 L/h of air are fed into the reaction mixture. The reaction mixture is heated to an internal temperature from 80 to 85° C. Samples are collected at regular intervals and analyzed by gas chromatography. After 6 h, the conversion of GMA into GCMA is 68.9%. The mixture comprises (disregarding components that do not pass through the GC) 68.41 area % of GCMA and 30.9 area % of GMA. The sum of the by-products is 0.69 area %. The selectivity is 99%. The reaction solution is colorless. The conversion of GMA into GCMA can be seen to occur considerably more slowly at ambient pressure in the absence of a suitable solvent.

Example C2

A round-bottomed flask equipped with jacketed coil condenser, magnetic stirrer, thermometer, $CO_2$ inlet, and with pressure equalization is charged with 7 mg of PTZ and 2.08 g of triethylamine. To this is added 41.5 g of GMA and 4.75 g of KI. $CO_2$ (approx. 2 L/h) and 0.5 L/h of air are fed into the reaction mixture. The reaction mixture is heated to an internal temperature from 70 to 74° C.

Samples are collected at regular intervals and analyzed by gas chromatography. After 7 h, the conversion of GMA into GCMA is 84.4%. The mixture comprises (disregarding components that do not pass through the GC) 79.21 area % of GCMA and 14.7 area % of GMA. The sum of the by-products is 5.97 area %. The selectivity is 93%. The reaction solution is orange.

Example C3

A round-bottomed flask equipped with jacketed coil condenser, magnetic stirrer, thermometer, $CO_2$ inlet, and with pressure equalization is charged with 17 mg of PTZ and 4.35 g of triethylamine. To this is added 42 g of GMA and 7.2 g of KI. $CO_2$ (approx. 2 L/h) is fed into the reaction mixture. The reaction mixture is heated to an internal temperature from 71 to 72° C. Samples are collected at regular intervals and analyzed by gas chromatography. After 28 h, the conversion of GMA into GCMA is 99.26%. The mixture comprises (disregarding components that do not pass through the GC) 91.07 area % of GCMA and 0.68 area % of GMA. The sum of the by-products is 8.14 area %. The selectivity is 91.8%.

The reaction mixture is worked up. The flask contents are mixed with 10 ml of ethyl acetate, transferred to a separating funnel, and extracted with 30×30 ml of water. The combined aqueous phases are extracted with 20 ml of ethyl acetate. The combined organic phases are then extracted again with 20 ml of saturated NaCl solution. After phase separation, the organic phase is dried over sodium sulfate, filtered, and washed with dichloromethane. The filtrate is concentrated under reduced pressure. 50.4 g of a brown solution is obtained in a purity of 93.9%. The yield is 94.5%. The Hazen color value was no longer measurable. The iodine color value is 23.

The invention claimed is:

1. A process for preparing glycerol carbonate methacrylate comprising reacting glycidyl methacrylate with carbon dioxide in the presence of a catalyst and a solvent,
wherein
the catalyst is potassium iodide, the solvent is acetonitrile, one or more monoalcohols, or any desired mixture of acetonitrile and one or more monoalcohols, and the reaction of glycidyl methacrylate with carbon dioxide is carried out at a pressure from 0.5 to 1.5 bar.

2. The process according to claim 1, wherein the reaction temperature is 50 to 100° C.

3. The process according to claim 1, wherein the pressure is 0.8 to 1.5 bar.

4. The process according to claim 1, wherein the process is a batchwise process.

5. The process according to claim 1, wherein the monoalcohol is ethanol, n-propanol, isopropanol, n-butanol, sec-butanol, isobutanol or tert-butanol.

6. The process according to claim 1, wherein the total amount of solvent used is 0.1 to 50 percent by weight based on the total amount of glycidyl methacrylate used.

7. The process according to claim 1, wherein the solvent is acetonitrile and the total amount of solvent used is 2 to 40 percent by weight based on the total amount of glycidyl methacrylate used.

8. The process according to claim 1, wherein the molar ratio between the total amount of catalyst used and the total amount of glycidyl methacrylate used is 0.005:1 to 0.5:1.

9. The process according to claim 1, wherein carbon dioxide as the carbon dioxide-containing gas is fed into the reaction mixture comprising the catalyst, the solvent, GMA that has not yet reacted, and optionally any GCMA already formed, and/or into the gas space above the reaction mixture.

10. The process according to claim 9, wherein the carbon dioxide-containing gas is fed in continuously.

11. The process according to claim 1, wherein an oxygen-containing gas is fed into the reaction mixture comprising the catalyst, the solvent, GMA that has not yet reacted, and optionally any GCMA already formed, and/or into the gas space above the reaction mixture.

12. The process according to claim 1, wherein the reaction of glycidyl methacrylate to glycerol carbonate methacrylate takes place in the presence of a stabilizer and the stabilizer is phenothiazine, one or more phenolic compounds, one or more N-oxyls or any desired mixture of the abovementioned stabilizers.

13. The process according to claim 1, wherein the reaction mixture resulting from conversion of most of the glycidyl methacrylate used into glycerol carbonate methacrylate is worked up and the workup comprises one or more extraction steps and/or one or more distillation steps.

14. The process according to claim 13, wherein the workup includes, in addition to one or more extraction steps and/or distillation steps, the addition of one or more acids.

15. The process according to claim 14, wherein the acid is phosphinic acid and/or phosphoric acid.

16. A process for preparing glycerol carbonate methacrylate comprising reacting glycidyl methacrylate with carbon dioxide in the presence of a catalyst and a solvent, wherein
the solvent is acetonitrile, one or more monoalcohols, or any desired mixture of acetonitrile and one or more monoalcohols, and
the catalyst consists of potassium iodide,
and the reaction of glycidyl methacrylate with carbon dioxide is carried out at a pressure from 0.5 to 5 bar.

* * * * *